(12) United States Patent
Thompson et al.

(10) Patent No.: US 8,288,320 B2
(45) Date of Patent: Oct. 16, 2012

(54) METHODS FOR PREPARING GRANULAR WEED CONTROL PRODUCTS HAVING IMPROVED DISTRIBUTION OF AGRICULTURALLY ACTIVE INGREDIENTS COATED THEREON

(75) Inventors: Harold E. Thompson, Powell, OH (US); Robert D. Baker, Westerville, OH (US)

(73) Assignee: OMS Investments, Inc., Los Angeles, CA (US)

( * ) Notice: Subject to any disclaimer, the term of this patent is extended or adjusted under 35 U.S.C. 154(b) by 1297 days.

(21) Appl. No.: 11/906,894

(22) Filed: Oct. 4, 2007

(65) Prior Publication Data

US 2009/0093368 A1    Apr. 9, 2009

(51) Int. Cl.
*A01N 39/02*    (2006.01)
(52) U.S. Cl. ...................................................... 504/323
(58) Field of Classification Search .................. 504/323; 118/20, 24, 62, 303
See application file for complete search history.

(56) References Cited

U.S. PATENT DOCUMENTS

| | | | |
|---|---|---|---|
| 4,117,801 A * | 10/1978 | Dannelly et al. ................. | 118/20 |
| 4,213,776 A | 7/1980 | Giilck et al. | |
| 5,006,158 A | 4/1991 | Carter et al. | |
| 5,354,742 A | 10/1994 | Deming et al. | |
| 5,680,993 A | 10/1997 | McCracken et al. | |
| 5,843,203 A | 12/1998 | Lindsay et al. | |
| 5,965,487 A | 10/1999 | Flahive | |
| 5,965,490 A | 10/1999 | Johnson et al. | |
| 6,022,829 A | 2/2000 | Mito | |
| 6,039,781 A | 3/2000 | Goertz et al. | |
| 6,189,260 B1 | 2/2001 | Kusey et al. | |
| 6,274,570 B1 | 8/2001 | Vogt et al. | |
| 6,297,197 B1 | 10/2001 | Fields et al. | |
| 6,303,814 B1 | 10/2001 | Johnson et al. | |
| 6,408,568 B1 | 6/2002 | Kusey et al. | |
| 6,417,140 B1 | 7/2002 | Patel | |
| 6,579,831 B1 | 6/2003 | Harwell | |
| 6,584,633 B2 | 7/2003 | Chute et al. | |
| 6,607,146 B1 | 8/2003 | Alness et al. | |
| 6,711,850 B2 | 3/2004 | Yelanich et al. | |
| 6,825,151 B2 | 11/2004 | Harwell | |
| 6,890,889 B1 | 5/2005 | Wichert et al. | |
| 6,924,250 B2 | 8/2005 | Cornes | |
| 6,962,894 B1 | 11/2005 | Glock | |
| 7,115,545 B1 | 10/2006 | Witschel et al. | |
| 2003/0013612 A1* | 1/2003 | Asrar et al. ................... | 504/359 |
| 2003/0141378 A1* | 7/2003 | Raehse et al. .................. | 239/13 |
| 2005/0096226 A1 | 5/2005 | Stock et al. | |
| 2007/0021305 A1* | 1/2007 | Baker ........................... | 504/348 |
| 2008/0103048 A1* | 5/2008 | Radabaugh et al. .......... | 504/234 |

OTHER PUBLICATIONS

Kogan et al., Dew and Spray Volume Effect on Glyphosate Efficacy, Weed Technology 15: 590-593 (2001).*
Notification of Transmittal of the International Search Report and the Written Opinion of the International Searching Authority, or the Declaration, dated Dec. 12, 2008.

* cited by examiner

*Primary Examiner* — Johann Richter
*Assistant Examiner* — Thor Nielsen
(74) *Attorney, Agent, or Firm* — Hunton & Williams LLP

(57) ABSTRACT

A method for improving the distribution of agriculturally active ingredients on the surface of granules includes preparing a sprayable liquid solution of at least one agriculturally active ingredient, and applying the sprayable liquid solution on the granules by spraying the liquid solution in atomized form onto the surface of the granules to provide a coating on the surface of the granules which enables substantially all of the agriculturally active ingredient on the granule to be solubilized by the naturally occurring moisture present on the foliage of a treated weed for absorption into the cells of the treated weed when the granules are applied thereto.

17 Claims, No Drawings

METHODS FOR PREPARING GRANULAR WEED CONTROL PRODUCTS HAVING IMPROVED DISTRIBUTION OF AGRICULTURALLY ACTIVE INGREDIENTS COATED THEREON

BACKGROUND OF THE INVENTION

1. Field of the Invention

The present invention relates generally to methods for preparing granular weed control products and, more particularly, to methods for improving the distribution of agriculturally active ingredients on such granular products.

2. Description of Related Art

Granular weed control products have been known in the consumer lawn industry which utilize systemic herbicides such as 2,4-D and MCPP-p for foliar application to broadleaf post-emergent weeds such as dandelions for purposes of killing the weeds. The active ingredients used in preparing these products are generally applied to inert carriers or fertilizer granules as a solid powder or a liquid solution. The level of active ingredient (AI) applied to the granular material is generally based on a specific total weight percentage of the entire product formulation. Normally, the resulting granular materials are then applied to a treated weed by using a spreader such as a broadcast spreader to spread the granules on the surface of the weed in a manner such that the individual granules or particles adhere to moist foliage in order to solubilize the active ingredient (AI), thus allowing it to enter the weed cells and kill the plant.

When a homogeneous sample of a typical weed control product is analyzed for active ingredient (AI) content the overall weight percentage obtainable is the key parameter of focus. However, the distribution of the active ingredient (AI) on the surface of the granules is generally not evaluated or specifically controlled.

As a result of this lack of distribution control, some granules have active ingredient (Ai) coatings with thicknesses and/or concentrations greater than can be solubilized by available moisture which, in most cases, comprises morning dew. The literature suggests that a moderate morning dew, during the spring time can deposit on average 30 mg/cm$^2$ of water, with a thickness of about 0.3 mm. This factor is generally not taken into consideration when determining how AI is applied to the fertilizer and inert carrier surface.

However, since weeds transport the available active ingredient (AI) into their cell structure on the basis of a concentration gradient, the amount of active ingredient (AI) that can be solubilized will be transported into the weed. To the contrary, if a granular or particulate product has a thick coating of active ingredient (AI) and there is insufficient moisture available to dissolve or solubilize the excess active ingredient, that excess amount of active ingredient will not be transported into the weed and will be essentially lost for purposes of treating the plant.

Such active ingredient loss can lead to inconsistent and generally lower weed control and inefficient utilization of active ingredients. Thus, in view of the problems encountered in controlling the distribution of active ingredient on the granular surfaces, many prior weed control formulations have included significantly greater concentrations of active ingredient than would be necessary if processes had been available for controlling the distribution of active ingredient on the granular surface.

Agricultural formulations can be applied to plants in the form of solids, solutions, emulsions, suspensions, dispersions and the like, and are used in agriculture for applying agriculturally active chemicals to plants, soil, insects and the like. Among typical agricultural chemicals are pesticides such as herbicides, insecticides, fungicides, growth regulators and the like. Other typical agricultural chemicals include plant nutrients and micronutrients.

In particular, agricultural formulations containing herbicides either as solid powders or liquid solutions can be applied to granular material and the herbicides coated on the granules to be applied to weed foliage to control the weed plants. Normally, the coated granules are applied either in a liquid spray application or in a granular solid application to moist weed foliage using a spreader such as a broadcast spreader, with the individual granules desirably adhering to the moist foliage to solubilize the active herbicidal ingredient, allowing the active ingredient to enter the weed cells and to kill the plant.

Exemplary of relevant prior art in this field is U.S. Pat. No. 5,006,158 which discloses that diverse active herbicidal compounds or salts disclosed therein can be formulated as granules of relatively large particle size, as wettable powders, as emulsifiable concentrates, as powdery dusts, as flowables, as solutions or as any of several other known types of formulations, depending upon the desired mode of application. The formulations containing the actives are disclosed to contain as little as about 0.5% to as much as about 95% or more by weight of active ingredient. A herbicidally effective amount of the actives is disclosed as depending upon the nature of the seeds or plants to be controlled and the rate of application varies from about 0.01 to approximately 10 pounds per acre, preferably from about 0.02 to about 4 pounds per acre.

Granular formulations wherein the actives are carried on relatively coarse particles as disclosed in U.S. Pat. No. 5,006,158 are usually applied without dilution to the area in which suppression of vegetation is desired. Typical carriers for such granular formulations as described in U.S. Pat. No. 5,006,158 include sand, fuller's earth, attapulgite clay, bentonite clays, montmorillonite clay, vermiculite, perlite and other organic or inorganic materials which absorb or which may be coated with the toxicant. These granular formulations are normally prepared to contain about 0.1% to about 25% of active ingredients which may include surface-active agents such as heavy aromatic naphthas, kerosene or other petroleum fractions, or vegetable oils; and/or stickers such as dextrins, glue or synthetic resins.

In U.S. Pat. No. 6,890,889, herbicidal formulations comprising agriculturally active ingredients in combination with an adjuvant system were disclosed to optimize post emergent activity on broadleaved weeds in corn. The preferred adjuvant system to optimize weed control and minimize crop response was disclosed to be a crop oil concentrate (COC). Other adjuvant systems for use in the formulation may comprise liquid compositions such as methylated seed oil (MSO), urea ammonium nitrate (UAN) and ammonium sulfate (AMS). No granular formulations are disclosed.

In Published U.S. Patent Application US 2005/0096226, herbicidal compositions useful for controlling weeds in growing crops such as maize (corn) comprising triketone products including mesotrione in combination with an organic phosphate, phosphonate or phosphinate adjuvant were disclosed which can be prepared as a pre-mix concentrate for formulation in various forms including granular formulations with typical carriers such as sand, fuller's earth, attapulgite clay, bentonite clays, montmorillonite clay, vermiculite, perlite and other organic or inorganic materials which absorb or which can be coated with the active compound.

Thus, when a typical weed control product is analyzed for active ingredient content, the overall weight percentage of active ingredient (AI) obtainable from the product normally is the key parameter considered. However, the distribution of the active ingredient on the surface of the granules has generally not been evaluated or specifically controlled and methods for adequately providing such control have not been available. This lack of distribution control in the production processes has resulted in significant quantities of granules having active ingredient coatings with thicknesses and/or concentrations greater than the level that can be solubilized by the available moisture, which in most cases is the morning dew. The literature suggests that moderate morning dew in the spring in the United States can deposit on average 30 mg/cm$^2$ of water with a thickness of about 0.3 mm.

In foliar treatments, plants transport active ingredients into their cell structure based on a concentration gradient and only the amount of active ingredient that can be solubilized will be transported into the weed. Thus, if a granule has a thick coating of active ingredient and if there is insufficient moisture on a treated leaf to dissolve the available active ingredient present in the coating, the excess active ingredient in the coating will not be transported into the cell structure of the plant for purposes of enhancing the weed killing effect of the applied granular product.

In this regard, it should be noted that in addition to the economic disadvantages resulting from waste of active ingredients when excess concentrations of such active ingredients are applied on the foliar surface of a weed in order to assure maximum intake of solubilized actives, governmental restrictions in the U.S. and elsewhere must also be taken into consideration concerning the amount of active ingredient that can be applied for weed control. Such governmental regulations may preclude the use and/or sale of products which will provide excessive application rates of actives ingredients when applied to weed foliage.

Thus, it has been a continuing problem in the art to provide methods for production of granular weed control products having relatively uniform distribution of active ingredients applied on the granules. In the absence of such methods, significant economic and functional problems have been encountered with the granular products produced employing methods which do not provide adequate distribution control capabilities. Such lack of distribution control can result in products that exhibit inconsistent and generally lower weed control and inefficient utilization of active ingredients including use of significantly greater concentrations of the active ingredients to achieve desired levels of weed control and these quantities may exceed governmental standards.

It would be advantageous to provide methods for producing granular agricultural products having improved control of the distribution pattern of active ingredients on such granular products.

Additionally, it would be advantageous to provide methods for improving the distribution of active ingredient (AI) on the surface of a weed control granule enabling reduction of the thickness of the active ingredient coating.

It also would be advantageous to provide methods for minimizing the potential for AI supersaturation in a granular weed control product and maximizing transport of the active ingredient (AI) on the granular product into the plant cells to cause effective kill of treated weeds.

SUMMARY OF THE INVENTION

Accordingly, it is an object of the present invention to provide methods for producing granular agricultural products having improved distribution of agriculturally active ingredients on the surface of the granules.

It is another object of this invention to provide methods for controlling the thickness of coatings applied on the surface of agriculturally active granular products to promote the transport of the active ingredient on the granules into the cells of treated weeds.

Another object of this invention is to provide methods for producing agriculturally active granules having controlled distribution of active ingredients on the granular surface, the granules being adapted for spray application onto foliar surfaces of weeds.

A further object is to provide methods for spraying atomized solutions of agriculturally active ingredients onto the surface of granules in a manner such that the distribution of the agriculturally active ingredients on the granular surface is controlled to enable enhanced transport of the active ingredient into the cell structure of a plant; such as a weed, treated with the resulting granular product.

In particular, it is an object of this invention to provide methods for improving the distribution of agriculturally active ingredients applied on the surface of granular substrates by spraying liquid solutions containing at least one agriculturally active ingredient on granules such as fertilizer granules, inert agriculturally acceptable granules and the like and mixtures thereof through nozzles which atomize at least a portion of the sprayed liquid solutions enabling the atomized droplets of the liquid solutions to be deposited on the granular surface at a controlled deposition rate and, most preferably, in a desired controlled distribution pattern such as a nonlinear, non-rectangular pattern.

Another particular object of this invention is to provide methods for dispensing a liquid solution containing at least one agriculturally active ingredient onto a granular substrate to form an agriculturally effective minimum coating thickness on the substrate by spraying the liquid solution through a nozzle onto the granular substrate at a certain deposition rate, preferably about 30-40 grams per second, and in a manner such that at least a portion of the sprayed solution is atomized and a coating is formed on the granular substrate at a sufficient thickness to enable substantially all of the agriculturally active ingredient on the granular substrate to be solubilized by naturally occurring moisture when the coated granules are applied to weed foliage such as the leafs of broadleaf weeds.

In this regard, it has been found that by improving the distribution of the active ingredient on the surface of the granules and by reducing the thickness of the active ingredient coating, the potential for active ingredient supersaturation is minimized and transport of the active ingredient into the weed cells is maximized.

Accordingly, a higher probability of delivering a lethal dose of active ingredient exists employing weed control products produced in accordance with the present invention in view of the higher levels of active ingredient transported into treated leaf cell structures whereby a greater percentage of treated weeds, such as broadleaf weeds, are killed at a given active ingredient total formulation concentration on the granules.

DETAILED DESCRIPTION OF THE INVENTION

In accordance with the present invention, granular herbicidal products for use in controlling weeds in a turfgrass, for example, are provided comprising agriculturally active ingredients coated on granular substrate materials wherein the granular substrates are solid fertilizer granules, inert solid carrier materials and the like and mixtures thereof. In a preferred embodiment, the solid fertilizer granules are organic or inorganic nitrogen-containing compounds.

Furthermore, in accordance with the present invention, a sprayable liquid solution containing at least one agriculturally active ingredient is prepared and the solution is spray coated, preferably through a particular nozzle configuration, onto a granular surface such as a fertilizer granule, an inert granular substrate and the like and mixtures thereof, at a prescribed deposition rate to provide a desired coating thickness and percentage active ingredient coverage of the granular surface. The sprayable liquid solution may comprise a solution of the active ingredient in a solvent or may constitute the active ingredient per se in a molten state.

Preferably, the liquid solution is sprayed through nozzles in a manner such that at least a portion of the liquid is atomized and the liquid is applied onto the granular surface in a desired coating thickness and at a desired deposition rate. In this regard, the level of atomization of the liquid solution spray is primarily dependent on the droplet size and, in a preferred embodiment of this invention, the preferred range of mean volume droplet diameters (MVD) should be about 100 to about 200 microns.

The thickness of the coating of active ingredient applied on the surface of the granular substrates herein will depend on a variety of factors. However, it has been found that a minimum effective coating thickness of active ingredient to be deposited on the granules to achieve optimal results when the coated granules are applied on weed foliage should be about 5.00 micrometers ($\mu m$) and the maximum active ingredient coating thickness should not exceed about 15.00 micrometers ($\mu m$) for best weed control results. In preferred embodiments of this invention the thickness of the coating should range from about 2 to about 10 micrometers ($\mu m$) to produce a granular product which is effective in accordance with this invention to reduce the potential for supersaturation and to enable an optimal amount of active ingredient to enter into the leaf cells of a treated plant.

The term "deposition rate" as employed herein refers to the rate at which the active ingredient is applied to the surface of the substrate granules and, preferably should be in a range of about 3.7 to about 5.0 grams per second of spray solution applied on the granules when the travel rate of the granules through the spray zone is about 30 to about 40 grams per second. The term "spray zone" as employed herein refers to the area on which atomized liquid from a spray nozzle orifice makes contact with the surface of a granular substrate. The geometry or shape of the spray zone is determined by the nozzle design (i.e., full cone, hollow cone, flat spray and the like). Most preferably, the ratio of solution spray to granule travel rate should range from about 6:1 to about 8:1 to achieve the most effective deposition rate for active ingredient coating. The travel rate of the granule surface is controlled by the fluidization rate and retention time of the granule processing equipment. The granule processing equipment can be a continuous or batch blender, fluidized bed, and or rotating drum. In this regard, it should be noted that the thickness of the coatings on the granule may be controlled by the retention time of the granules in the spray zone and/or the travel rate of the granules through the spray zone at a constant liquid deposition rate.

Atomization of the liquid spray solution is achieved in accordance with this invention by spraying the solution of active ingredient through spray nozzles that have small orifices to create hydraulic pressure that is significant enough to break apart the fluid stream as it is delivered to the substrate. It has been found in accordance with this invention that nozzles which break apart the solution stream and form a cone shaped spray deposition pattern on the granular substrate are within the preferred parameters. In this regard, preferred nozzle designs for use in the methods of the present invention are various known nozzle designs including hollow cone designs, full cone designs, air assist designs and the like. However, certain of the known spray nozzle designs such as flat spray nozzles have been found to be ineffective for use herein.

Specifically, full cone design nozzles provide spray patterns on sprayed substrate surfaces in the spray zone that may be doughnut shaped, round, square or oval and the spray patterns are completely filled with droplets. Such nozzles are hydraulically atomized nozzles which contain an internal vane or deflector that breaks apart the sprayed solution and imparts controlled turbulence to the liquid prior to a nozzle orifice to form the spray pattern. The spray shape such as the doughnut shaped or circular spray pattern minimizes overspray while creating a large liquid spray area and, thus, increases application coating efficiency and uniformity. An example of this nozzle design is the UniJet®TG0.4 Spray Nozzles, sold by Spraying Systems Co., which develops droplets with a mean volume droplet diameter (MVD) of 180 microns.

Hollow cone type nozzles which are also hydraulically atomized nozzles provide hollow cone spray patterns that are essentially circular rings of liquid which are generally formed by use of an internal grooved vane or deflector immediately upstream from a nozzle orifice, or by an inlet formed in the nozzle tangential to a whirlchamber. The internal deflector design or whirling liquid feature of the hollow cone type nozzles helps generate a small liquid droplet size and a relatively large spray area. An example of this type of nozzle design is the UniJet® TX2 Spray Nozzles, sold by Spraying Systems Co., which produces droplets with a mean volume droplet diameter (MVD) of 105 microns.

Another nozzle design useful for spraying agriculturally active ingredients in accordance with this invention is the air assist design. This design uses a high pressure of about 8-12 pounds per square inch (PSI) air stream, which is externally combined with the spray liquid solution to break apart the stream into fine droplets. The greater the compressed air flow pressure, the smaller the liquid droplet size for a constant liquid flow rate. This nozzle design allows an increase in the solution delivery rate while maintaining small droplet sizes equal to the hollow cone or full cone designs, by increasing compressed air pressure, thus allowing greater granular travel rates passing through the spray zone of about 200-260 grams per second.

Nozzles having characteristics within the above parameters as described herein atomize the active ingredient liquid into droplets to a size 50% smaller than a flat spray nozzle design. The flat spray nozzle is also a hydraulically atomized liquid design. However, flat spray nozzle designs such as the VeeJet TP8001 nozzles sold by Spraying Systems Co., which do not include internal deflectors to assist in breaking up the liquid flow have been found to create a relatively small rectangular pattern on the surface of the spray zone and to develop a liquid droplet having a mean volume droplet diameter (MVD) of about 233 microns, have been found to be ineffective for use in the methods of the present invention.

In this regard, it should be noted that, under similar conditions at pressures of about 100 pounds per square inch (PSI), hollow cone design (TX2) type nozzles develop droplets with a mean volume droplet diameter (MVD) of 105 microns and full cone design (TG0.4) type nozzles develop droplets with a mean volume droplet diameter (MVD) of 180 microns as opposed to the unacceptable flat spray type nozzle designs which develop droplets with a mean volume droplet diameter (MVD) of 233 microns.

Thus, the use of full cone and/or hollow cone and/or air assist nozzles to spray active ingredients onto granular substrate surfaces in the methods of the present invention for preparing granular weed control products have been found to produce desired active ingredient coating or coverage areas on such granular substrate surfaces and, also, to provide desired deposition rates for application of such coatings.

Preferred agriculturally active ingredients for use in preparing the sprayable liquid solutions to be used in the methods of this invention are any pesticidal agents capable of being solubilized and applied in liquid form for treatment of weeds including any one or more of the known herbicidal compositions. Examples of the wide variety of suitable herbicides for use herein are described in U.S. Pat. Nos. 4,213,776; 5,965,487; 5,965,490; 6,022,829; 6,297,197; 6,303,814; 6,417,140; 6,579,831; 6,890,889; 6,924,250; 6,962,894 and 7,115,545.

Most preferable herbicides for use in the methods of this invention are 2,4-D (2,4-dichloro-phenoxyacetic acid) and MCPP-p (2-(2-methyl-4-chlorophenoxy)propionic acid). As noted, the preferred form of the most preferred herbicides are acidic, and these active ingredients can be dissolved in solvents such as hexylene glycol, aliphatic hydrocarbon mixtures sold by Shell Oil Company under the trade name "ShellSol D-100" or aliphatic hydrocarbon mixtures sold by Exxon Chemicals Company under the trade name "Exxsol D110" and methyl esters such as biodiesel and the like and mixtures thereof. Preferably spraying temperatures ranging from about 70° F. to about 195° F. are employed in accordance with the present invention.

In a further embodiment of the present invention, the sprayable liquid solution for use in preparing granular weed control products may comprise the agriculturally active ingredient per se in a molten state, for example, for use within a spraying temperature range of 200° F.-285° F.

In the methods of the present invention, the granular substrates onto which the liquid solutions containing at least one agriculturally active ingredient are sprayed preferably comprise fertilizer granules and may comprise any type of fertilizer core compound(s). Known chemical fertilizers including potassium nitrate, potassium sulfate, urea, ammonium nitrate, monopotassium sulfate, ammonium phosphate and the like and fertilizers obtained from compounding these fertilizer materials may be employed as the granular substrates in the present invention. Also, fertilizers containing micronutrients or trace elements may be used as the granules. Examples of suitable UF fertilizers for use herein are described generally in U.S. Pat. No. 6,039,781 for example. Also, other examples of fertilizers useful herein are described in U.S. Pat. No. 6,579,831.

Further illustrative fertilizers which can be employed as a granular composition for use in the present invention include a wide variety of fertilizer granules, particles or pellets (which are referred to collectively herein as fertilizer granules) such as organic and inorganic nitrogen-containing compounds comprising urea, urea-formaldehyde condensation products, amino acids, ammonium salts and nitrates, potassium salts (preferably chlorides, sulfates, nitrates) and phosphoric acid and/or salts of phosphoric acid. Also, it should be noted that the fertilizer granules suitable for inclusion in the present mixtures may also contain micronutrients, such as iron, manganese, magnesium, boron, copper, zinc and the like.

The physical forms of the fertilizers to be employed in the methods of the present invention include granules and extruded particles. Fertilizer granule sizes, preferably, should range from about 1.0 to about 5.0 mm diameter (most preferably, about 1.5-3.0 mm). Extruded particle sizes preferably should range from about 0.6 to about 7.0 mm diameter (most preferably, about 1.0-3.0 mm). Particle length preferably should range from about 0.6 to about 10.0 mm (most preferably, 1.0-5.0 mm).

Preferably, the chemical analysis of the fertilizer component to be used in the present methods should range from about 1 to about 40% by weight elemental nitrogen (N) (most preferably, about 15-36% by weight); about 1 to about 30% by weight phosphorous as $P_2O_5$ (most preferably, about 1-27% by weight); and about 1 to about 20% by weight potassium as $K_2O$ (most preferably, about 3-15% by weight). The micronutrient content of the fertilizer ingredient, preferably, should range from about 1 to about 20,000 ppm (parts per million).

In a preferred embodiment of this invention a methyleneurea fertilizer is utilized as the granular substrate for the weed control products so that when the product is applied to control weeds, for example, in turf applications, the fertilizer portion of the product will be useful in treating the turf while the selected herbicidally active ingredient will control the weeds.

Examples of inert agriculturally acceptable granular substrates useful in the methods of the present invention are those described in U.S. Pat. No. 6,579,831. Additionally, suitable inert solid carrier materials for use herein include any of a variety of organic and/or inorganic materials, which may be coated with the agriculturally active ingredient and that have been appropriately ground/fractionated/sized. Suitable organic materials include agglomerated cellulosic carrier granules such as Biodac®, sold by Kadant GranTek, Inc., which is described in U.S. Pat. No. 5,843,203. Other suitable organic materials include such manufactured, not screened, products having a structure consisting of a wood fiber core such as EcoGranules™ sold by Cycle Group, Inc.; compressed coir granular products such those described in U.S. Pat. Nos. 6,189,260; 6,408,568 and 6,711,850; corncobs; peanut hulls; processed paper pulp; sawdust and the like whereas suitable inorganic materials include limestone, diatomaceous earth, gypsum, sand, vermiculite, perlite, fuller's earth and clays such as attapulgite clays, bentonite clays, montmorillonite clays and mixtures of these substrates.

In preferred embodiments of this invention, methods are provided for applying a liquid AI solution which, for example, may contain a systemic herbicide such as 2,4-D and MCPP-p on a granular substrate such as a methyleneurea fertilizer, a physical fertilizer blend or an encapsulated fertilizer or an inert substrate or other substrate. Preferably, the liquid AI solution is sprayed on the granular substrate through hydraulically atomized spray nozzles having designs such as full cone or hollow cone structures. These full cone or hollow cone nozzle designs have been found to atomize AI solution droplets to a size which may about 50% smaller than would be achieved employing a flat spray nozzle design. In an alternate embodiment, air assist spray nozzles can be utilized and a deposition rate or material travel rate passing through the spray zone of 200-260 gm/second is attained. The AI coverage area employing any of these application nozzles should equal a sufficient width and length to cover the entire surface of the granular substrate being coated in the spray zone.

Employing the herein described spray nozzle designs, it has been found that the AI coating thickness is minimized, reducing the potential for supersaturation to occur and allowing increased levels of AI to enter treated leaf cells. Preferably, the resulting AI coating thickness should range from about 2.0 to about 10.0 micrometers (μm).

The following specific examples are presented to further illustrate and explain certain aspects of the present invention. However, the Examples are set forth for illustration only, and are not to be construed as limiting on the present invention. In the following examples, all percentages and parts are by weight unless otherwise specified.

In addition, the coating thicknesses described in the following Examples are based on the percentage of active ingredient coverage generated by spraying liquid active ingredient containing solutions through particular nozzle design arrangements. In this regard, it was found that hollow cone nozzle designs provided 46.17% coverage of active ingredient on the sprayed granules while air assist nozzle designs provided 35.31% active ingredient coverage. Based on these findings, the coating thicknesses were calculated as being 4.88 μm and 6.38 μm, respectively, which thicknesses were within the desired coating thickness ranges for the desired weed control products. To the contrary, the active ingredient coverage achieved by spraying through flat spray nozzles resulted in active ingredient coverage of 16.84% providing calculated coating thicknesses of 13.37 μm which were significantly greater than the desired level of active ingredient coating thicknesses required to avoid the potential for supersaturation when the products are applied to weeds.

Example 1

Four separate sprayable liquid solution samples were prepared by dissolving 70% by weight 2,4-D and 30% MCPP-p active ingredients at a temperature of 265 F. The mixture was heated and agitated for a period of 20-30 minutes in steam jacketed vessel to ensure uniformity. Using a continuous Pilot Plant granulation system, an NPK methyleneurea based fertilizer substrate was prepared at a nutrient analysis of 28-2-3. The process of manufacturing to fertilizer using molten methyleneurea resin generated a granular fertilizer substrate at a temperature of 85-95 F. The warmed methyleneurea fertilizer was then continuously fed into a blender with retention time such that the material travel rate could be maintained between 30-40 grams per second through the active ingredient spray zone comprising the total area of the continuous blender where active ingredient could be applied to the granular surface. The molten active ingredient solution was pumped, on a continuous basis, through a steam jacketed piping system, in order to reach the spray nozzle area at a temperature consistent with the steam jacketed vessel temperature. The pumping system controlled the rate of active ingredient application such that delivery was maintained at 3.7-5.0 grams per second, as well as generate a final product analysis with 1.22% 2,4-D and 0.61% MCPP-p to manufacture four samples of a commercially available Turf Builder® Plus 2 (with reduced 'P') granular fertilizer (marketed by The Scotts Miracle Gro Company, Marysville, Ohio, USA) to produce four coated weed control product samples.

Four different AI spray nozzle designs were employed for spraying the liquid solution onto the granular fertilizer substrate. The first nozzle design was a flat spray design which displayed a rectangular spray pattern and provided almost no liquid atomization (i.e., MVD of 233 microns). The second nozzle design was a full cone (MVD 180 microns) design and the third nozzle design was a hollow cone (MVD 105 microns) design. The full cone and the hollow cone designs displayed circular spray patterns and provided significantly greater liquid atomization when compared to the flat spray design. The fourth nozzle design employed was an air assist pneumatically operated assembly (pressure orifice) having two fluid zones, one for active ingredient (AI) containing solution and the other for heated compressed air, which provided an atomized, fine spray. During each experiment, the liquid AI deposition rates, as well as the granular substrate material travel rates, were held constant in the targeted ranges of about 3.7 to 5.0 grams per second of spray solution applied on the granules at a granule travel rate of about 30 to about 40 grams per second through the spray zone.

Once the production of the four weed control product samples was completed, a small sample of each was taken and placed into a scanning electron microscope (SEM) with an energy dispersive spectrometer (EDS) detector. Once the sample was placed in the SEM and testing initiated, the electron beam collided with the sample surface and generated backscatter electrons which help form the image of the sample surface. As a result of the collisions, x-rays, having energy levels that are characteristic of specific elements and in there respective spatial arrangement on the sample surface, were also generated.

The EDS detector measures the energy from element specific x-rays generated during the electron beam scan without losing the element's spatial arrangement on the sample surface. Quantitative weight percentages of each element on the surface were estimated by measuring the total amount of each characteristic X-ray energy generated as the electron beam collided with the sample. Since 2,4-D and MCPP-p have elemental chlorine (Cl) in their formula, that element was used to determine the spatial arrangement of each active ingredient compound on the granule surface. Using this technique on samples that were not treated with active ingredient, it was determined that the surface of the methyleneurea fertilizer granules were almost completely covered with elemental nitrogen (N), oxygen (O), and carbon (N). Based on that finding, the percentage of the surface covered with active ingredient was estimated by first measuring the total quantitative weight of nitrogen (N) detected and then measuring the quantitative weight of chlorine (Cl), without altering their spatial arrangement on the sample surface. The ratio of the chlorine wt % and the nitrogen wt % were used to estimate the percentage of active (AI) coverage on the particles.

This procedure was replicated three times for each sample evaluated and a summary of the results achieved by application of the liquid solutions on the granular fertilizer substrates as described herein including the weight percents of elemental nitrogen and chlorine, the ratio of elemental chlorine to elemental nitrogen and the coating thicknesses calculated from elemental maps is shown in the following table for each nozzle design.

|  | Full Cone Spray Nozzles | Hollow Cone Spray Nozzles | Air Assisted Spray Nozzles | Flat Spray Nozzles (Controls) |
| --- | --- | --- | --- | --- |
| Wt % N | 35.29 | 30.16 | 34.09 | 37.51 |
| Wt % Cl | 7.93 | 13.71 | 11.93 | 6.29 |
| Cl:N Ratio | 0.2267 | 0.4617 | 0.3531 | 0.1684 |
| Thickness of Coating, μm | 9.93 | 4.88 | 6.38 | 13.37 |

The tabulated results demonstrate that a coating thickness in the range of about 2-10 μm was achieved by spraying atomized droplets of the liquid solution onto the substrates using the full cone, the hollow cone and the air assisted nozzle designs. With the testing indicating that the air assist and the hollow cone designs provided the best overall active ingredient distribution on the granular substrate surfaces.

To the contrary, the flat spray nozzles (designated as Controls) which caused rectangular spray patterns without atomization of the sprayed droplets, resulted in coatings of 13.37 µm which were significantly greater than the desired coating thickness range so that these samples could result in active ingredient (AI) supersaturation when the product is applied for weed control which would cause active ingredient (AI) waste.

Example 2

Coated fertilizer granules prepared in accordance with the procedures of Example 1 by spraying of the liquid solutions on the fertilizer granules described therein using the indicated spray nozzle designs, were spread by using a laboratory spreader device, onto dandelion and white cover weeds in early morning and with naturally occurring dew in Marysville Ohio. The test began in mid-September and the percentage weed control achieved four weeks after application was noted and tabulated as follows:

| Percentage Weed Control Achieved By Spray Application of Coated Granules (% Control) | | | | | | | |
|---|---|---|---|---|---|---|---|
| Full Cone Spray Nozzles | | Hollow Cone Spray Nozzles | | Hollow Cone Spray Nozzles | | Flat Spray Nozzles (Controls) | |
| Dandelion | White Clover | Dandelion | White Clover | Dandelion | White Clover | Dandelion | White Clover |
| 78.3 | 69.4 | 90.8 | 74.6 | 91.7 | 60.4 | 66.1 | 39.5 |

As demonstrated by the percentage weed control results shown in the table, coated granular products having the active ingredient (AI) incorporated in the liquid solution sprayed onto the Turf Builder® Plus 2 (with reduced 'P') granular fertilizer surface through the flat spray Control nozzles which provided a rectangular spray pattern without atomization when applied to the indicated plants in the early morning in Marysville Ohio and having naturally occurring dew thereon, resulted in only 66.1% control of dandelion plants and 39.5% control of white clover plants, whereas products produced by spraying atomized droplets of the liquid solution onto the fertilizer granules using the full cone, and the hollow cone designs resulted in 78.3% to 91.7% control of dandelion plants and 69.4% to 74.6% control of white clover plants.

This significant improvement in weed control demonstrated in this example was unexpected and attributable to the combination of the sprayable liquid solution employed and the atomizing effect of the nozzles through which the liquid solutions were applied to the granules, particularly, when the generally circular spray pattern demonstrated when full cone and hollow cone nozzles were employed.

Although the invention has been described in its preferred forms with a certain degree of particularity, it is to be understood that the present disclosure has been made by way of example only. Numerous changes in the details of the compositions and ingredients therein as well as the methods of preparation and use will be apparent without departing from the spirit and scope of the invention, as defined in the appended claims.

What is claimed is:

1. A method of making a granular weed control product comprising:

spraying atomized droplets of a molten liquid comprising no solvent and at least one agriculturally active ingredient onto the surface of the granules at a deposition rate sufficient to provide a coating on the surface of the granules having a thickness enabling substantially all of the agriculturally active ingredient on the granule to be solubilized by naturally occurring moisture present on foliage of a weed treated with the granules and to be absorbed into cells of the foliage of the weed when the granules are applied to the weed.

2. The method of claim 1, wherein the thickness of the coating is in a range of about 5.00 µm to about 15.00 µm.

3. The method of claim 1, wherein the atomized droplets are sprayed through a full cone or hollow cone nozzle at a deposition rate in a range of about 3.7 to about 5.0 grams per second of molten liquid applied on the granules at a travel rate of the granules through a spray zone of about 30-40 grams per second.

4. The method of claim 3, wherein the ratio of granule travel rate to deposition rate ranges from about 6:1 to about 8:1.

5. The method of claim 1, wherein the atomized droplets are sprayed through an air assisted spray nozzle to provide hydraulically atomized droplets at a deposition rate of about 200-260 grams per second.

6. The method of claim 1, wherein the granules are fertilizer granules, inert agriculturally acceptable granular substrates, or mixtures thereof.

7. The method of claim 6, wherein the inert agriculturally acceptable granular substrate is an organic material, an inorganic materials, or mixtures thereof.

8. The method of claim 7, wherein the organic material comprises agglomerated cellulosic carrier granules, wood fiber core granules, compressed coir granules, corncobs, peanut hulls, processed paper pulp, sawdust, or mixtures thereof.

9. The method of claim 7, wherein the inorganic material comprises limestone, diatomaceous earth, gypsum, sand, vermiculite, perlite, fuller's earth, clay, or mixtures thereof.

10. The method of claim 1, wherein the at least one agriculturally active ingredient is a systemic herbicide.

11. The method of claim 10, wherein the systemic herbicide is 2,4 dichlorophenoxyacetic acid.

12. The method of claim 10, wherein the systemic herbicide is 2-(2-methyl-4-chlorophenoxy)propionic acid.

13. The method of claim 1, wherein the molten liquid is applied on the surface of the granule through at least one atomizing spray nozzle.

14. The method of claim 1, wherein the weed is a broadleaf weed.

15. A granular weed control product made by the method of claim 1.

16. A method of controlling weeds comprising applying the weed control product of claim 15 to the weeds.

17. A method of making a granular weed control product comprising:

spraying atomized droplets of a molten liquid consisting essentially of at least one agriculturally active ingredient onto the surface of the granules at a deposition rate sufficient to provide a coating on the surface of the granules having a thickness enabling substantially all of the agriculturally active ingredient on the granule to be solubilized by naturally occurring moisture present on foliage of a weed treated with the granules and to be absorbed into cells of the foliage of the weed when the granules are applied to the weed.

* * * * *